United States Patent [19]

Leser

[11] Patent Number: 4,694,158

[45] Date of Patent: Sep. 15, 1987

[54] CONTACTLESS INSPECTION OF OBJECTS WITH FEEDBACK TO HIGH SPEED MANUFACTURING DEVICE

[75] Inventor: Jacques Leser, Lunel, France

[73] Assignee: Verrerie du Languedoc et Cie, Vergeze, France

[21] Appl. No.: 782,336

[22] Filed: Oct. 1, 1985

[30] Foreign Application Priority Data

Oct. 2, 1984 [FR] France ............... 84 15117

[51] Int. Cl.$^4$ .......... B07C 5/00; B07C 5/02; B07C 5/342
[52] U.S. Cl. ............... 250/223 B; 250/205; 356/240; 209/524
[58] Field of Search ............ 250/205, 223 R, 223 B, 250/224; 356/239, 240; 65/163, 164, DIG. 13; 209/523, 524; 364/473, 478

[56] References Cited

U.S. PATENT DOCUMENTS

| | | | |
|---|---|---|---|
| 3,762,907 | 10/1973 | Quinn et al. | 364/473 X |
| 3,946,212 | 3/1976 | Nakao et al. | 235/151.13 |
| 4,145,204 | 3/1979 | Farkas et al. | 65/DIG. 13 X |
| 4,247,317 | 1/1981 | Wood et al. | 65/DIG. 13 X |
| 4,254,364 | 3/1981 | Flint et al. | 250/205 X |
| 4,354,865 | 10/1982 | Poad et al. | 65/29 |
| 4,475,937 | 10/1984 | Nitschke | 364/473 X |
| 4,476,533 | 10/1984 | Daudt et al. | 364/473 |
| 4,494,656 | 1/1985 | Shay et al. | 250/223 B X |
| 4,529,429 | 7/1985 | Wood | 65/163 X |
| 4,529,912 | 7/1985 | Northrup et al. | 250/205 X |
| 4,533,053 | 8/1985 | Hammond et al. | 250/205 X |
| 4,533,854 | 8/1985 | Northrup | 250/205 X |

FOREIGN PATENT DOCUMENTS

| | | |
|---|---|---|
| 0059575 | 2/1982 | European Pat. Off. . |
| 0059572 | 2/1982 | European Pat. Off. . |
| 0060160 | 2/1982 | European Pat. Off. . |
| 0100239 | 2/1984 | European Pat Off. ............... 65/164 |
| 2475424 | 2/1980 | France . |
| 2087549 | 10/1981 | United Kingdom . |
| 2135452 | 2/1984 | United Kingdom . |

OTHER PUBLICATIONS

Article from Glass Technology, vol. 22, of Jun. 3, 1981, by W. Sanders Entitled: Solid State Optics For Sidewall and Dimensional Inspection of Glassware.

Primary Examiner—Eugene R. Laroche
Assistant Examiner—David Mis
Attorney, Agent, or Firm—Beveridge, DeGrandi & Weilacher

[57] ABSTRACT

Method for performing the automatic contactless inspection of objects manufactured at a high speed by an automatically controlled machine, in particular high-temperature glass objects, the objects moving in front of an optical measuring device, consisting in illuminating the moving objects with a non-coherent white light, sensing the transmitted light by means of an optical sensor (5) provided with a linear measuring strip (2) comprising a plurality of receptor photodiodes (3), the strip (2) being arranged with its longitudinal axis perpendicular to the movement of the objects (6) and to the focal point of a focusing lens (9), and storing the result of the sensing operation for a given number of objects.

13 Claims, 7 Drawing Figures

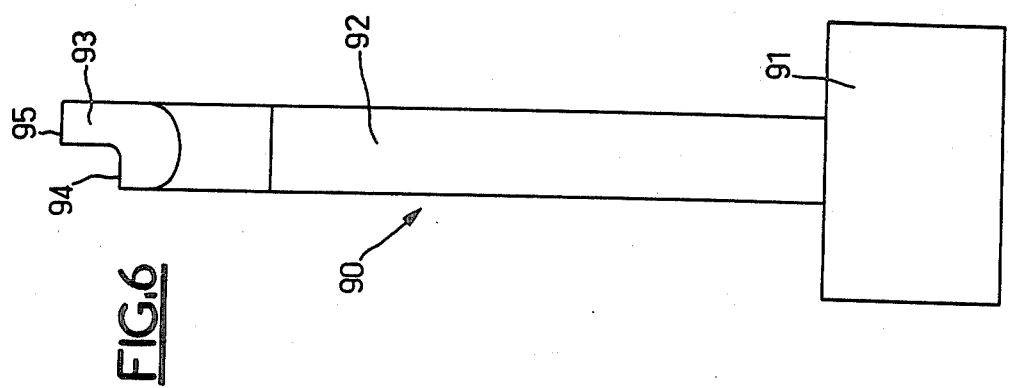
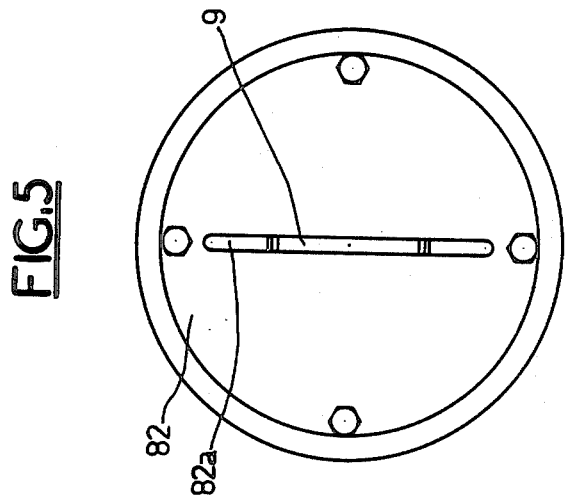

CONTACTLESS INSPECTION OF OBJECTS WITH FEEDBACK TO HIGH SPEED MANUFACTURING DEVICE

The present invention relates to a method and a device by means of which it is possible to perform the contactless inspection of objects manufactured automatically at high speed. The invention relates in particular to the manufacture of glass objects at a high temperature. It is possible, as a result of the method according to the invention, to adjust the automatic control cycle of the manufacturing machine in accordance with the measurement performed, so as to improve production.

The invention may be used, for example, to improve the quality of molded-glass bottles manufactured in particular by means of injection-blow molding.

The high-speed mass production of objects requires the organization of efficient and low-cost quality control procedures. These inspection procedures are usually performed at the end of the production line by means of mechanical, electrical or optical operations performed at several stations which are arranged in succession and each of which checks one or more characteristics of the product's specifications. The mechanical inspection procedures which require contact cannot always be used because they may have the tendency to adversely affect the condition or nature of the manufactured product. Thus, in particular molded objects cannot be inspected when hot since mechanical contact is likely to cause permanent deformation.

Optical inspection procedures, which are sometimes used, consist in placing one or more photoelectric barriers along the path of the manufactured objects. Each photoelectric barrier consists of a single light beam which, if necessary, is modulated and screening of which gives rise to a signal which may be used to supply data relating to the shape of the product. However, these optical measurements require the use of precise conveying means for the products, since slight displacement of the manufactured product while it is being moved after manufacture, for example on a conveyor belt, gives rise to a large margin of error in the measurement.

The automatic high-speed manufacture of glass or plastic objects molded at a high temperature, for example in injection-blow molding machines, requires, in particular, numerous and varied checks. This applies in particular to the manufacture of bottles where it is important to eliminate any bottle with certain defects constituting a danger for the end user.

Hence, in the manufacture of glass bottles, for example by means of multisection automatic injection-blow molding machines, from time to time the appearance of defects may be noted and the bottles in question must be rejected. These consist, for example, of inclusions in the material which form unmelted grains, filaments of glass between the two walls of the bottle (a defect which is commonly called "birdswing"), a surplus of material on the collar of the neck, etc.

Other equally important defects generally require that the bottles which have them be eliminated. In particular, defects in the verticality, which prevent filling by automatic filling machines, the appearance of microscopic cracks or a reduced thickness in certain parts of the walls, etc. Finally, certain secondary defects, such as specks, folds, marking defects, etc., must be avoided as far as possible so as to ensure uniform quality of the manufactured products.

The machines for manufacturing these objects and, in particular, automatic injection-blow molding machines with a plurality of sections are generally controlled by means of a programmable automaton equipped with a microprocessor and memory systems. The machine may be controlled by varying the parameters stored in the microprocessor so as to modify the multiple operating characteristics for each of the molds in the different sections of the machine. Usually, control is effected by manually modifying the data on the keyboard of the microprocessor controlling the automatic machine.

The necessary quality checks are always carried out on the products after cooling. As seen above, in fact, it has always been considered hitherto that the checking procedures could not be carried out under the right conditions, before cooling of the products. Thus, for example, the glass bottles manufactured in machines of the abovementioned type, upon leaving the molds, have a temperature which is generally regarded as too high to allow a proper check to be performed. Moreover, the material of which the bottles are made is still relatively weak and risks breaking before undergoing the annealing process which precedes cooling.

The checking procedures which, in this application, must be carried out on all the manufactured bottles in accordance with the client's requirements are therefore performed on the bottles after cooling, i.e. approximately one hour after manufacture. It will be appreciated that the appearance of systematic defects or an increase in certain particular defects does not make it possible, in practice, to perform an immediate correction on the machine. Moreover, it is extremely difficult to determine with certainty the exact origin of objects which have defects. Therefore, it is not possible to intervene in a particular section of the manufacturing machine by means of the microprocessor, so as to eliminate with certainty the defects which have appeared.

Hitherto, therefore, it has been decided more often than not to destroy the bottles which have the greatest defects and to perform rough manual adjustment of the automatic control system of the manufacturing machine, which eliminates only some of the defects and involves a long response time.

The object of the present invention is to overcome these difficulties and to make it possible to perform the automatic contactless inspection of objects manufactured at high speed.

The invention also relates to a method whereby the result of the measuring operation performed on the objects is used to modify the manufacturing process immediately, so as to avoid the reproduction of the defects detected.

The invention relates, moreover, more particularly to the inspection of molded products in the hot state, in particular plastic or glass containers or bottles, inspection being performed without contact, as soon as the products leave the manufacturing machine.

In this particular application, an object of the invention is also to provide the possibility of adjusting manufacturing process retrospectively by supplying the programmable automaton controlling the molding machine with data resulting from the measurements performed, so as to modify the operational characteristics of the machine and prevent the reappearance any of the defects detected.

The present invention relates to the application of this general method for automatically inspecting the quality of glass bottles in the hot state as well as to the automatic operation of the molding machine in accordance with the results of the measurements performed.

The invention also relates to inspection, in the hot state, of the height of molded-glass bottles as well as to automatic operation of the manufacturing machine in order to eliminate the defects detected.

The invention also relates to verification of the distance between molded objects manufactured at high speed, in particular bottles which are manufactured by means of injection-blow molding and which are moved on a conveyor belt upon leaving the machine, as well as to operation of the manufacturing machine so as to maintain a constant distance.

According to the invention, the method for performing the automatic contactless inspection of objects manufactured at high speed by means of an automatically controlled machine, in particular high-temperature glass objects, the objects moving in front of an optical measuring device, consists in illuminating the moving objects, sensing the transmitted light by means of an optical sensor provided with a linear measuring strip comprising a plurality of receptor photodiodes, the strip being arranged with its longitudinal axis perpendicular to the movement of the objects and to the focal point of a focusing lens, and storing the result of the sensing operation for a given number of objects.

This stored result can therefore be used by the operator to vary immediately the automatic control cycle of the manufacturing machine. Since measurement is performed preferably as soon as the product leaves the manufacturing machine, it is obvious that inspection is performed immediately after manufacture so that it is possible to modify very rapidly certain parameters of the manufacturing process, thereby avoiding the reproduction of any defects detected.

In a preferred variation of the method according to the invention, the result of the sensing operation is stored in a processor, which is itself connected to a programmable automaton controlling the manufacturing machine, so as to adjust the latter periodically in accordance with the stored data. In this case, manual action on the part of the operator is no longer necessary and the automatic measuring process enables immediate retrospective action to be taken, which tends to eliminate a defect which may have been detected.

Moreover, in a preferred manner of implementing the method according to the invention, the power supplied to the light source is regulated in accordance with the result of the sensing operation so as to avoid saturation of the photodiodes of the measuring strip.

According to a particular application of the method according to the invention, the objects are moved in linear fashion into a light beam, screening of the transmitted light is sensed, as each object moves past, by means of an optical sensor equipped with a linear strip comprising a plurality of receptor photodiodes, the strip being arranged with its longitudinal axis perpendicular to the movement of the objects and to the focal point of a focusing lens; the time difference between the signal thus sensed for a given passing object and a theoretical, stored signal for the said object is measured; the differences measured for a certain number of objects are stored and the automatic control system of the manufacturing machine is operated so as to modify the control parameters for regulating the distance between the objects.

In a preferred method of implementation, the measuring operation is initialized by moving a gauge, the characteristics of which are known, in front of the optical measuring device.

The contactless inspection device according to the invention, enabling the invention to be implemented, comprises a means of illumination, the intensity of which is regulated, a linear measuring strip comprising a plurality of receptor photodiodes, the longitudinal axis of the strip being perpendicular to the movement of the objects and the strip being arranged so that the objects move between the measuring strip and the means of illumination during measurement. The measuring strip is mounted at the focal point of a focusing lens. A processor receives the signals supplied by the measuring strip and stores them.

Illumination may be obtained by means of any kind of light. In a preferred method of implementation, use is made of a linear light source, the longitudinal axis of which is parallel to that of the measuring strip. Such a source advantageously consists of one or more fluorescent tubes supplied with electrical current, the intensity of which is regulated.

In order to avoid flickering of the light source, the current supplying the fluorescent tubes is, moreover, preferably a current alternating at a high frequency and more particularly at a frequency such that the tubes emit continuous light. To this end, the frequency must be greater than that at which the afterglow of the luminous discharge in the fluorescent tube ensures a constant light source.

In a preferred embodiment of the device according to the invention, the processor is connected to the automatic control system of the machine so as to be able to modify the manufacturing process in accordance with the results of the measurements.

The processor comprises preferably means for storing the signals arriving from different photodiodes of the measuring device and an output for controlling adjustment of power supplied to the illumination means in accordance with threshold corresponding to saturation of the photo-diodes.

In an advantageous practical embodiment of the device according to the invention, the latter comprises a transmitter unit associated with the measuring strip, a comparator receiving both the signals emitted by the photodiodes of the measuring strip and the threshold signals, and a series/parallel shift register associated with a digital/analog converter connected to the comparator so as to supply the latter with threshold signals. The comparator thus emits an output signal each time the signal emitted by a photodiode exceeds the threshold signal supplied.

The optical sensor is preferably protected from the external environment. To this end, the device comprises a protective housing receiving the measuring device, the focusing lens and the electronic connection components. One of the ends of the protective housing forms a dedusting chamber provided with a closing wall with an open slot parallel to the measuring strip.

A sleeve advantageously surrounds the protective housing, defining an intercalated cooling space which communicates with the dedusting chamber which is thus subjected to an excess pressure.

The invention will be more clearly understood by examining a few embodiments described by way of a completely non-limiting example and illustrated by the attached drawings in which:

FIG. 5 is an external end view of the protective housing of the optical sensor shown in FIG. 4;

FIG. 6 is an external view of a gauge used for initializing measurement;

The examples in the description which follows relate to the general method of the invention as applied to the automatic inspection of glass bottles manufactured by means of injection-blow molding in an automatically controlled machine with a plurality of individual sections each provided with two molds. This application also includes adjustment of the molding machine's operation in accordance with the results of the measurements performed.

It will be understood, of course, that the method according to the invention can be applied to any other process involving the manufacture of objects in large quantities.

Figure 1:
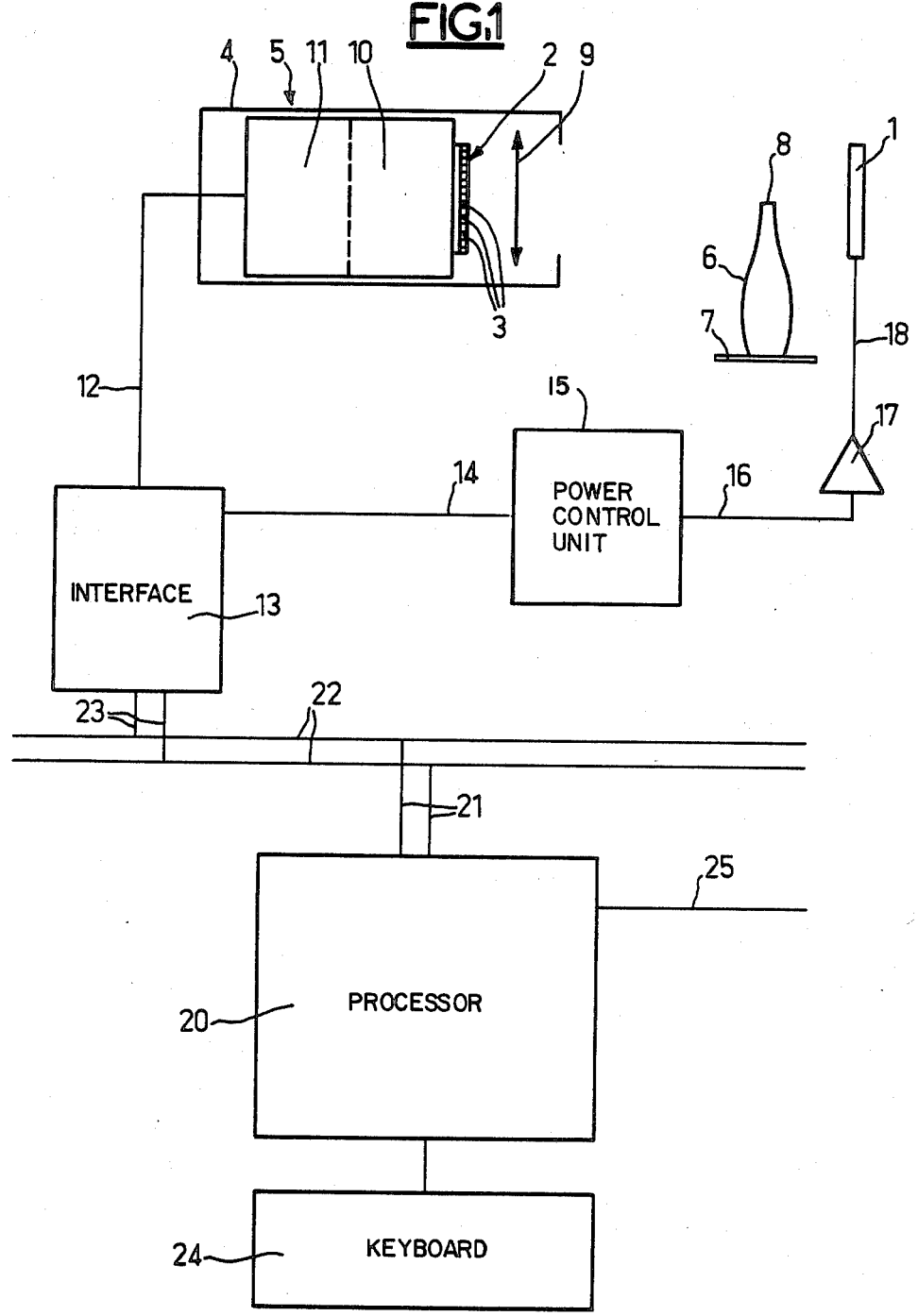
FIG. 1 is a schematic overall view of the device according to the invention.

As shown in FIG. 1, the device comprises a white-light illumination means 1, which may consist advantageously of one of more fluorescent tubes, a linear measuring strip 2 provided with a plurality of photodiodes 3 and mounted inside a protective housing 4, the entire assembly defining an optical sensor 5.

The bottles to be inspected, such as the bottle 6, move on a conveyor belt shown schematically at 7, perpendicularly to the plane of the Figure. The longitudinal axis of the measuring strip 2 is therefore perpendicular to the movement of the bottles 6. It will be noted that, in the example of embodiment, the light source 1 advantageously consists of a fluorescent tube, the longitudinal axis of which is parallel to that of the measuring strip 2. A protective cover, not shown in the Figure, may advantageously be provided so as to partially block the light source 1 and keep it pressurized under compressed air so as to prevent the penetration of dust.

In the arrangement shown in FIG. 1, the upper part of the neck 8 of the bottle 6 is substantially aligned with the center of the measuring strip 2. In fact, FIG. 1 shows, by way of example, the method according to the invention as applied to measurement of the height of the bottles 8 so as to detect any defect as regards height. Of course, in the case where the method is used to detect another type of defect, the optical sensor 5 and the light source 1 will be arranged differently so that the defect in question can be better assessed.

The most important feature concerning application of the method according to the invention is that the longitudinal axis of the measuring strip 2 is perpendicular to the movement of the bottles 8 so that, as a result of the combination of the linear arrangement of the photodiodes 3 with the perpendicular movement of the bottles 8, it is possible to obtain, using a simple means consisting of the measuring strip 2, an analysis and the recognition of shapes by means of digital processing of the images supplied by the photodiodes in accordance with the movement of the bottles.

Moreover, the measuring strip 2 is arranged at the focal point of a focusing lens 9.

The signals emitted by the photodiodes 3 are amplified or processed by the amplifier unit 10. The sensor 5 has, moreover, a transmitter-receiver unit 11 connected via the line 12 to the interface 13 which operates, via the line 14, the supply and power control unit 15 of the light source 1. For this purpose, the supply control unit is connected via the line 16 to the amplifier 17 it-self connected via the line 18 to the lamp 1.

A processor 20 is connected via the lines 21, 22 and 23 to the interface 13. Dialogue with the processor 20 is possible by means of the keyboard 24. Moreover, the processor 20 is capable of sending control signals to the programmable automaton which controls the machine for injection-blow molding of the bottles 8 by means of the line 25.

Figure 2:
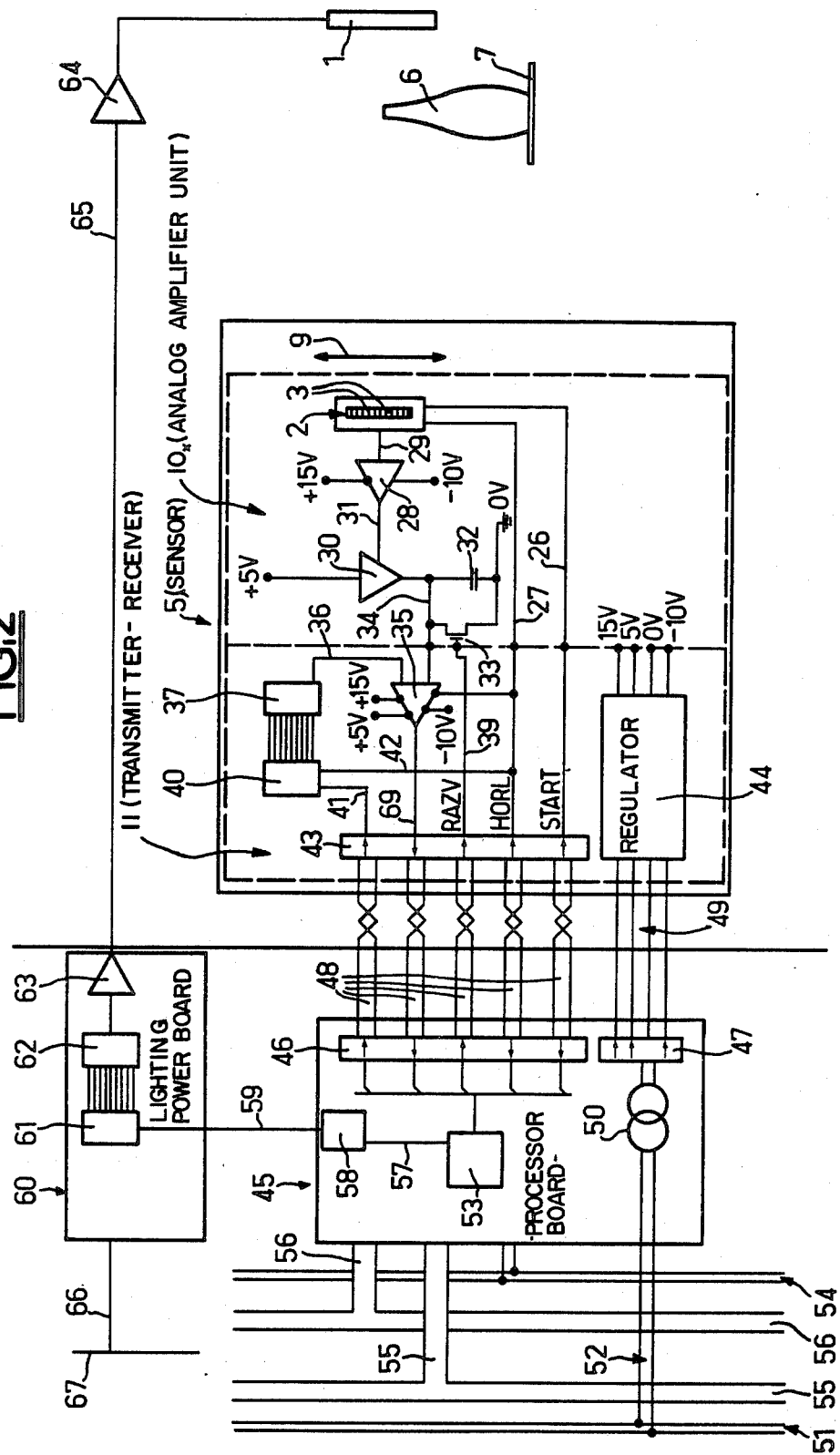
FIG. 2 shows schematically the main electronic components for processing the measuring signals.

With reference to FIG. 2, which shows most of the electronic components of the device shown in FIG. 1, the analog components have the same reference numbers.

The analog amplifier unit 10 receives the signals from the measuring strip 2 arranged, as already described, at the focal point of the lens 9. The network is supplied by two d.c. voltages, −10 and +5 volts, and two digital signals: the start signal conveyed by the line 26 and the clock signal conveyed by the line 27. The network generates streams of pulses synchronized with the start and clock signals amplified by the fast-acting operational amplifier 28 connected via the line 29 to the measuring strip 2. The signal emitted from the amplifier 28 is integrated in an integrating circuit comprising a voltage current converter 30 connected via the line 31 to the amplifier 28 and an integrating capacitor 32 at the terminals of which a fast-acting static switch 33 is connected.

The signal appearing at the output of the capacitor 32 on the line 34 supplies a fast-acting comparator 35 via one of its inputs. The threshold of this comparator is fixed by the output 36 of a digital/analog converter 37. Each time a pulse appears at the input of the capacitor 32, the latter is discharged by the static switch 33 supplied by a zero signal RAZV conveyed on the line 39.

The analog threshold of the digital/analog converter 37 is fixed by the digital value at the input itself defined by a serial transfer at the input of the shift register 40 with a series input and parallel output connected to the network via the link 41 and receiving the clock signal via the line 42.

The various emission and reception signals travel via a line transmission/reception module 43.

The assembly is further completed by a voltage regulator device 44.

The sensor 5 is associated with a processor board 45 which has a line transmission/reception system 46 connected to the transmitter-receiver 43 as well as a voltage preregulator device 47 connected to the regulator 44.

The sensor 5 is connected to the processor board via the cables 48 and 49 which comprise twisted pairs for the electrical signals (cables 48) and single wires for the power supply (cables 49).

The voltage preregulator 47 is supplied at a frequency of 400 Hz by means of a non-radiating toric transformer 50 connected to the 24-volt, 400 Hz main supply line, indicated by 51, by means of the line 52.

The processor board has a CPU 53 with a large RAM and a ROM, as shown in the Figure.

The processor board is connected to the 5-volt supply line indicated by 54 for supplying the integrated circuits. The processor board 45 is also connected to a local decision bus 55 and to a general data transfer bus 56.

The signals supplied by the CPU 53 are transmitted via the line 57 to a shaping unit 58 and then via the line 59 to a lighting power board indicated in its entirety by 60. The latter comprises a series/parallel shift register (designated 61) connected to a digital/analog converter 62. The output signal amplified by the power amplifier 63 is then transmitted by means of a voltage/frequency converter 64 connected via the line 65 to the light source 1. The lighting power board 60 is connected via the line 66 to the 30-volt lighting power line 67.

The voltage variation at the input of the converter 64 gives rise to variations in the brightness of the fluorescent tube 1. It is thus possible to regulate the power so as to avoid any harmful saturation of the photodiodes.

The converter 64 supplies the tube 1 with high-frequency current, for example of the order of 25,000 Hz, so as to use the afterglow of the luminous discharge inside the tube 1 in order to obtain a constant emission of light, i.e. without flickering.

Figure 3:
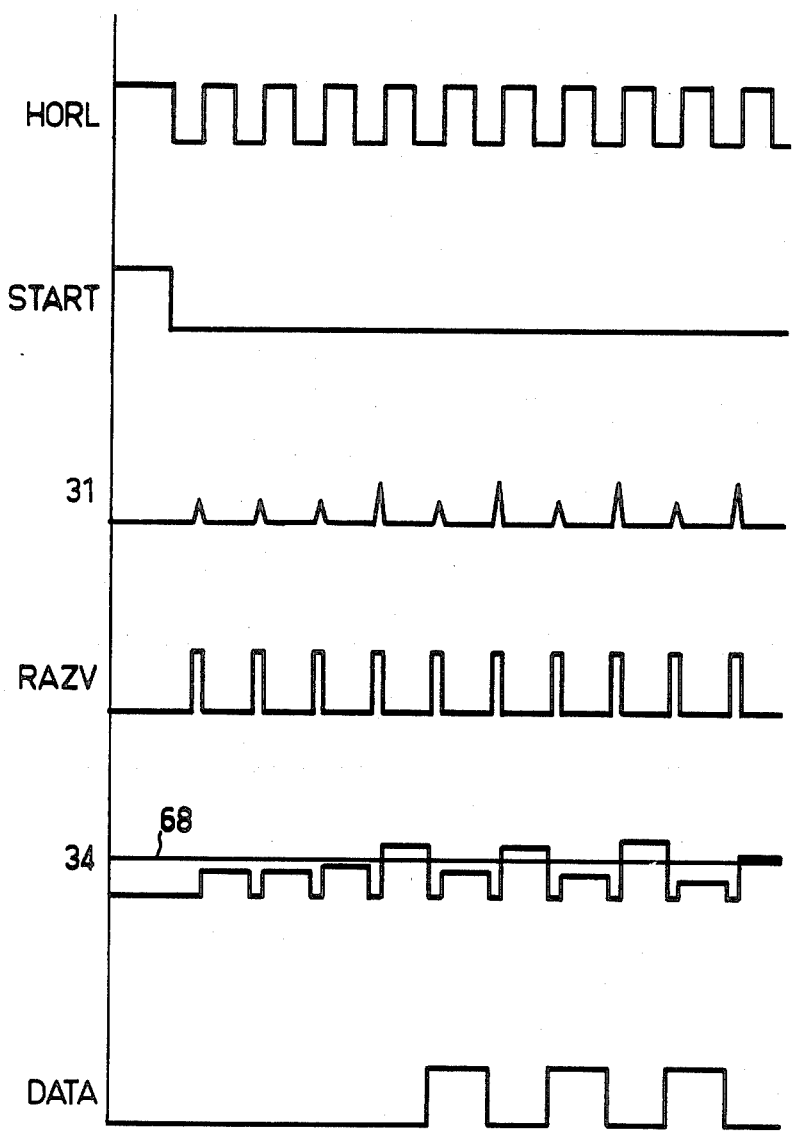
FIG. 3 shows the development in time of various signals appearing at certain points in the circuit shown in FIG. 2.

FIG. 3 shows the various operating signals of the sensor 5. The first signal at the top of the Figure is the clock signal which operates the shift register 40 of the photodiode network 2, together with the start signal which is the second signal down from the top of FIG. 3.

The signal appearing on the line 31 at the output of the amplifier 28 cannot be directly used. The signal RAZV applied to the grid of the switch 33 provides the signal appearing on the line 34. This signal enters the comparator 35 where it is compared with the threshold voltage 36 (straight line 68 in FIG. 3) so as to provide the signals marked "data" which are emitted from the comparator 35 and conveyed by the line 69. It is these digital signals which are then transferred to the processor board 45.

Figure 4:
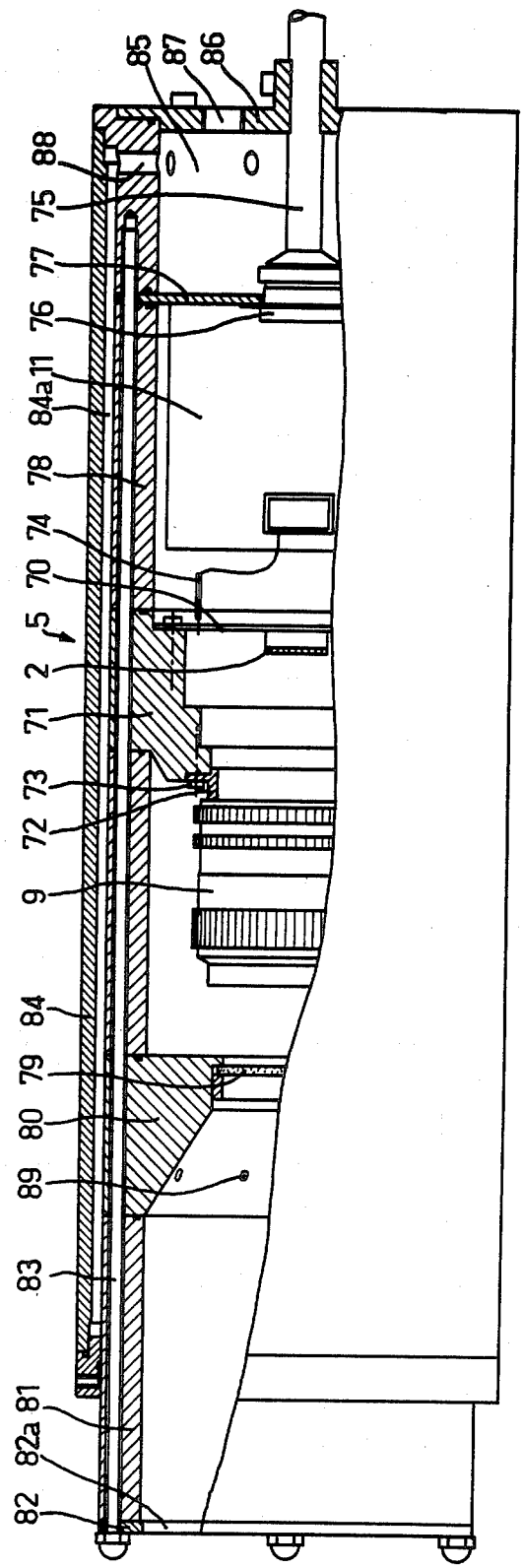
FIG. 4 is a sectional view of an example of embodiment of the optical sensor used in the device according to the invention, showing in particular the means ensuring protection against the environment.

FIG. 4 shows a practical embodiment of the sensor 5. In FIG. 4 we can see the focusing lens 9 and the strip of photodiodes 2 arranged in the focal plane of the lens 9. The strip 2 is directly fixed to the plate 70 screwed into the lens holder 71. The analog amplification and processing circuit is mounted on the plate 70. The lens 9 is fixed to the lens holder 71 by means of an adaptor ring 72 and by means of a screw 73. The amplified signals are transmitted via the connection 74 to the transmitter/receiver board 11. After conversion, the signals are transmitted via the electronic link-up cable 75, the end 76 of which is integral with a radial plate 77 mounted on the housing 78.

A heat-protection filter 79 arranged in a filter holder 80 is mounted in front of the lens 9. The photodiode strip 3 is, in fact, very sensitive to the presence of infrared rays. If the inspection is carried out on objects emitting radiation with a wavelength in the region of one micron, such as, for example, glass bottles after they have been removed from the mold, it is advisable to use such a filter so that this radiation does not disturb reception of the light rays emitted in the visible range by the source 1.

A dedusting chamber 81 with a cylindrical wall is mounted at the front end of the sensor 5. It has, as can be seen in FIG. 5, a front occluding wall 82 provided with an open slot 82a arranged on a diametral line.

The component assembly forming the sensor 5 is fixed by means of axial locking screws 83. A cylindrical sleeve 84 surrounds the housing of the sensor 5, leaving a space 84a.

A pressurized-air supply chamber, designated 85, is located at the rear of the sensor 5 and is defined at the rear by a frontal partition 86 provided with a pressurized-air inlet orifice 87. The air supplied via the orifice 87 enters the annular space 84a through the radial holes 88 and flows into this space, thereby cooling the sensor. Holes 89 provided in the filter holder 80 communicate with the space 84a and with the dedusting chamber 81, creating an excess pressure inside the latter. In this way, external dust is prevented from adversely affecting operation of the sensor.

So that measurement can be initialized and operation of the system started, use is made of a gauge device shown in FIG. 6 and designated 90 in its entirety. In the application described here by way of example, relating to bottles, the total height of the gauge 90 corresponds substantially to the height of a bottle. More precisely, it can be seen that the gauge 90 has a base 91 and a stem 92 at the top of which there is a projection 93 with half the thickness of the stem 92. A lower level 94 and an upper level 95 are thus defined. The difference in levels may be, for example, of the order of 20 mm. The average height of a high-temperature bottle, such as one leaving the manufacturing machine, is situated at an equal distance from the levels 94 and 95.

With reference to FIGS. 1 and 6, the device thus operates as follows. The gauge 90 is placed on the conveyor belt 1 so that the upper projecting part 96 provided with two surfaces 94 and 95 is situated face-on between the measuring strip 2 and the light source 1. During its movement in front of the sensor 5, the projecting part 93 therefore obscures, with its integral part located below the level 94, a certain number of photodiodes on the measuring strip 2. When the movement continues, more photodiodes are obscured by the integral part located below the level 95.

The emission, in succession, of these two signals, caused by the movement of a gauge 90 can thus be recognised by the processor and in particular by the CPU 53 (FIG. 2).

Under these conditions, when the gauge 90 passes by, the processor notes the time Te. Knowing also the time intervals which elapse between the manufacture of each bottle, the processor is able to deduce, taking into account the data relating to the initial position of the gauge, the exact origin of each bottle measured. In other words, the processor is able to pinpoint the section of the molding machine which has manufactured a given bottle on which a defect is detected. Consequently, the processor is also able to supply a control signal to the automaton monitoring the machine, so as to alter an operational characteristic in accordance with the defect detected for a given section of the molding machine.

In an application which consists in checking the height of the bottles manufactured, measurement is performed by determining the number of diodes which are obscured each time a bottle passes by. When measurement is actually performed, the instant when the measuring operation is carried out is also indicated and stored inside the processor. The actual height is calculated by the processor by determining the number of photodiodes obscured and using the exact height of the two levels 94 and 95 of the bottle gauge 90. The section of the molding machine which made a bottle of defective height is pinpointed by calculations based on the time when a given bottle passes by. So that light which may pass through the bottles will not lead to incorrect measurements, it is advisable to regulate the light, using an opaque object, in order to compensate for variations in the sensitivity of the sensor as well as variations in the brightness of the lighting. For this purpose, after each bottle has passed by, and the moment when it passes by has been recorded, the measuring frequency of the sensor 5 is doubled. In these circumstances, its light sensitivity is halved. At this point, and if there is no other bottle blocking its field of vision, the CPU 53 checks to see whether the level of the signal appearing on the line 34 at the input of the comparator 35 (FIG. 2) is greater or less than the chosen threshold. In the case where the level is less than the chosen threshold, the CPU transmits, via the power board 60, an additional voltage unit, thereby increasing the brightness of the light source 1. On the other hand, in the case where the level is greater, the CPU transmits a signal which tends to decrease the intensity of the light source 1.

Figure 7:
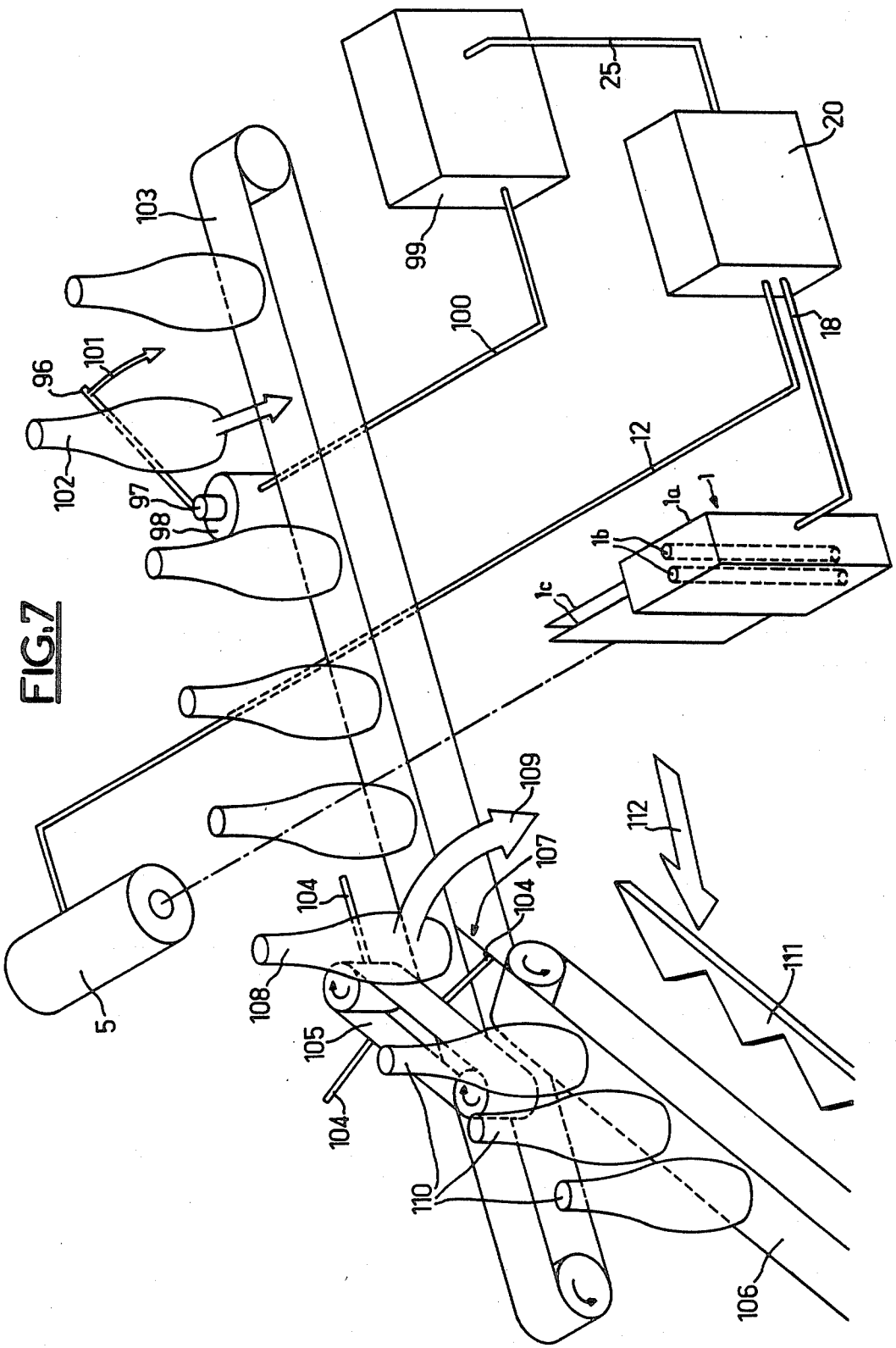
FIG. 7 is a schematic perspective view showing the invention as applied to measuring and verification of the distance between bottles leaving an injection-blow molding machine.

FIG. 7 illustrates the method according to the invention as used for another application, i.e. regulation of the distance between bottles leaving a molding machine.

The light source 1 and sensor 5 are shown. FIG. 7 shows, in schematic form, the protective cover of the light source 1 comprising two fluorescent tubes 1b, the longitudinal axis of which is perpendicular to the movement of the bottles, as in the case of the photodiode strip of the sensor 5. A light emission slot is defined between two parallel plates 1c. The whole cover 1a, which is open on the side where the abovementioned slot is located, is subjected to a compressed-air supply which flows out through the slot, thus ensuring the permanent removal of dust.

FIG. 7 shows schematically a thruster arm 96 integral with a pin 97 driven by a motor 98 operated by the processor 99 to which it is connected via the electrical line 100.

Of course, the molding machine, not shown in FIG. 7, has a plurality of molding sections. In each section there are two molds associated with a thruster arm 96. Each time a mold is opened, the thruster arm is actuated so as to rotate about the pin 97 in the direction of the arrow 101, thereby pushing the bottle 102, which has just been molded, onto the metal conveyor belt 103 which moves from right to left in FIG. 7.

The metal belt 103 extends over the entire length of the molding machine not shown in the Figure. As is known, this machine, which is for example an injection-blow molding machine, is supplied with parisons by a single feed device. The molds therefore operate in succession and the manufactured bottles are ejected in an order determined by a particular cycle stored in the computer 99. The various manufactured bottles arrive in succession on the belt 103. In the vicinity of the downstream end of the latter, the bottles are arranged behind each other with a certain distance in between.

In practice, the distance between each of the bottles is not absolutely uniform. Therefore, a mechanical regulating device is provided, consisting of a plurality of arms 104 integral with an endless belt 105 which, during their movement, take up each bottle in succession and move them from the metal belt 103 onto a second conveyor belt 106 which forms an angle in relation to the belt 103, a horizontal plate 107 allowing the bottles to pass from one belt to the other. In the case where a bottle is not located at a suitable distance, i.e. at a distance corresponding to the distance between the arms 104, these arms cause the bottle 108 to fall in the direction of the arrow 109 into a container where they are eliminated.

It is thus possible to obtain bottles 110 arranged at regular intervals on the conveyor belt 106. This regular interval is necessary so that the row of bottles 110 can be taken up by the thrusting member 111 which moves periodically in the direction of the arrow 112 and pushes an entire row of bottles 110 inside an annealing mold not shown in the Figure. At this stage in the manufacturing process, it is important for the distance between the bottles 110 to be perfectly uniform.

Hitherto, this regulating operation was performed, as stated above, by means of the arms 104, this giving rise to the elimination of a certain number of bottles such as the bottle 108, while these bottles might equally well not have any manufacturing defects other than being arranged at a non-uniform distance.

In order to overcome this difficulty, the device and the method according to the invention are used. It can be seen in FIG. 7 that the sensor 5 is arranged on one side of the row of bottles located on the belt 103, while the light source 1 is arranged on the other side. FIG. 7 also shows the connections 18 and 12 as well as the processor 20 connected to the computer 99 via the line 25.

The processor 20, which has previously been set by causing a bottle-gauge 90 moved by a thruster arm 96 from one of the machine sections to pass in front of the sensor 5, detects the moment when each of the bottles passes by during a manufacturing cycle. Knowing, moreover, the speed of movement of the belt 103, the processor 20 measures the time difference between the theoretical signal of a passing bottle and the actual signal. This time lag, which may be positive or negative, is stored on several occasions. The mean of these measurements is also stored. The stored signal advantageously has as many bytes as there are bottles in a cycle. In each byte, a certain number of bits are reserved for the absolute value of the position measurement, while one bit indicates the sign (plus or minus). Periodically, for example every two or three minutes, the buffer processor transmits the contents of its memory to the computer 99 so that the latter is able to operate, as required, the thruster arms 96. This operation is performed so that the contents of the memory tend towards zero, the system thus operating as a closed-loop controller.

Therefore, according to the method of the invention, it is possible to perform not only quality control in the hot state as soon as the product leaves the manufacturing machine, but also automatic adjustment by regulating retrospectively the actual operation of the manufacturing machine.

According to the method of the invention, shapes can be roughly recognized owing to the use of a plurality of photodiodes arranged in a linear strip perpendicular to the movement of the objects to be inspected.

Using any light source, it is possible to ensure complete illumination of the object whatever its shape and, therefore, to obtain a precise measurement by moving the object so that it obscures a certain number of photodiodes.

As a result of the invention, it is possible to carry out, in the hot state, a plurality of checks on the bottles. In particular, by analyzing the general shape of each bottle, it is possible to detect bottles which are stuck to each other or lying horizontally on the conveyor belt. It is also possible to detect, by analyzing the shape of the bottles, bottles which are too small or which are inclined in relation to the vertical. In all of the above cases, the defective bottles can be ejected and, if the incident is repeated for a given section of the manufacturing machine, direct retrospective action can be taken on the manufacturing machine so as to eliminate this incident. It is also possible, as a result of the invention, to count the number of bottles manufactured by each section and to measure directly the actual speed of the conveyor belt.

I claim:

1. A method of continuous contactless inspection of glassware articles and automatic control of the manufacturing process of said glassware articles comprising the following steps:

moving said glassware articles before substantive cooling and before any subsequent annealing step between an optical sensor means and a light source, said optical sensor means comprising a linear measuring strip of a plurality of receptor photodiodes and means for thermal protection of said sensor means, said strip having its longitudinal axis perpendicular to the movement of said articles, using said light source to illuminate one side of the entire surface of one said glassware articles while regulating said light source to avoid any flickering, storing data issued by said sensor means for a given number of glassware articles, and periodically controlling the manufacturing process in accordance with the stored data.

2. The method of claim 1, including the step of avoiding saturation of the diodes by regulating the power supplied to the source of illumination in accordance with the result of the sensing operation.

3. The method of claim 2, wherein the measuring frequency of the sensor is increased to reduce its light sensitivity after each article has passed by, comparing the signal received with a given threshold, increasing the power of the light source if the level is lower than the given threshold, decreasing the intensity of the light source if the level is greater than the given threshold.

4. The method according to claim 1 including the step of storing a theoretical signal which is a signal desired to occur when an article passes between the fluorescent light tube and the linear measuring strip, measuring the difference between the time of the stored theoretical signal and the time of a signal which is generated by the optical sensor means in response to the movement thereby of a glassware article, controlling the manufacturing process is by regulating the distance between the glassware articles.

5. Automatic inspection method as claimed in claim 4, including the step of producing the stored theoretical signal by moving a gauge with known characteristics in front of the optical sensor means.

6. An apparatus for continuous contactless inspection of glassware articles having a high temperature, said articles moving along a path at the output of automatically controlled manufacturing machine and before substantive cooling and any subsequent annealing of said glassware articles, comprising:

a fluorescent light tube capable of illuminating one side of the entire surface of one of said glassware articles, a linear measuring strip which includes a plurality of receptor photodiodes disposed perpendicular to the path of said articles and parallel to the longitudinal axis of said light tube, said linear measuring strip and said fluorescent light tube being on opposite sides of the path of said articles, a focusing lens having its focal point located at said strip, means for thermally protecting said focusing lens and said photodiodes comprising a housing having an open slot arranged parallel to said measuring strip and means for flowing pressurized air into said housing, a processor means for receiving signals supplied by the photodiodes of the measuring strip, means for regulating the intensity of said light tube at a frequency greater than the afterglow of said tube, means for connecting said processor means to an automatic control unit of the manufacturing machine so as to be able to modify the manufacturing process in accordance with the results of the measurements.

7. An apparatus according to claim 6, comprising several said fluorescent tubes enclosed inside said housing.

8. An apparatus according to claim 6, wherein the processor comprises means for storing signals emitted by each of the photodiodes of the measuring strip and an output for adjusting the power supplied to the fluorescent tube in accordance with a threshold corresponding to saturation of the photodiodes.

9. An apparatus according to claim 6, comprising a transmitter-receiver unit associated with the measuring strip and having a comparator receiving both a succession of signals emitted by the photodiodes of the measuring strip and a succession of threshold signals, and a series/parallel shift register associated with a digital/analog converter connected to the comparator so as to provide the latter with said threshold signals, the comparator emitting an output signal each time the signal emitted by a photodiode exceeds the threshold signal provided.

10. An apparatus according to claim 9, wherein the transmitter-receiver unit is provided with a switch for zeroing the signal received by the comparator from the photodiode.

11. An apparatus according to claim 6, wherein the housing includes a dedusting chamber, and a heat protection filter is mounted between the dedusting chamber and the lens.

12. An apparatus according to claim 6 wherein the housing includes a dedusting chamber, a sleeve surrounding the protective housing and defining a cooling space for circulating pressurized air, said cooling space communicating with the dedusting chamber whereby the dusting chamber is subjected to an excess pressure.

13. An apparatus according to claim 6 including a buffer processor capable of measuring the time difference between a theoretical signal which represents a desired time for an article to pass and an actual signal produced when an article passes, said buffer processor being capable of storing a mean value of the measurements performed on several articles, and means for transferring periodically the contents of the buffer processor to a control unit of a manufacturing machine so as to modify its operation to obtain a substantially uniform standard distance between the articles.

* * * * *